(12) United States Patent
Chardon-Bras et al.

(10) Patent No.: US 10,285,897 B2
(45) Date of Patent: May 14, 2019

(54) DEVICE, STRAP AND GARMENT FOR TREATING SKIN AND SUBCUTANEOUS TISSUE DISORDERS AND FOR REPAIRING SPORTS INJURY, AND METHOD FOR MAKING SAME

(75) Inventors: Maryvonne Chardon-Bras, Montpellier (FR); François Courtet, St Regis du Coin (FR)

(73) Assignee: THUASNE, Levallois-Perret (FR)

( * ) Notice: Subject to any disclaimer, the term of this patent is extended or adjusted under 35 U.S.C. 154(b) by 912 days.

(21) Appl. No.: 12/067,655

(22) PCT Filed: Sep. 22, 2006

(86) PCT No.: PCT/FR2006/002176
§ 371 (c)(1),
(2), (4) Date: Apr. 9, 2008

(87) PCT Pub. No.: WO2007/034090
PCT Pub. Date: Mar. 29, 2007

(65) Prior Publication Data
US 2008/0269654 A1    Oct. 30, 2008

(30) Foreign Application Priority Data
Sep. 22, 2005 (FR) .................... 05 09724

(51) Int. Cl.
| | |
|---|---|
| *A61F 5/00* | (2006.01) |
| *A61H 7/00* | (2006.01) |
| *A61F 13/08* | (2006.01) |
| *A61F 13/00* | (2006.01) |

(52) U.S. Cl.
CPC ............. *A61H 7/002* (2013.01); *A61F 13/08* (2013.01); *A61F 2013/00327* (2013.01); *A61F 2013/00604* (2013.01); *A61F 2013/00634* (2013.01); *Y10T 156/1089* (2015.01)

(58) Field of Classification Search
CPC ............ A61F 13/08; A61F 2013/00327; A61F 2013/00604
USPC ........ 602/6, 46, 53, 900, 41, 60, 75, 76, 77; 156/297, 292, 300, 301, 302; 428/221, 428/71, 323; 442/224, 373, 393, 417
See application file for complete search history.

(56) References Cited

U.S. PATENT DOCUMENTS

| | | | |
|---|---|---|---|
| 4,377,159 A * | 3/1983 | Hansen | ........................... 602/53 |
| 5,175,046 A * | 12/1992 | Nguyen | ................ A61F 13/535 |
| | | | 428/198 |
| 5,356,372 A | 10/1994 | Donovan et al. | |
| 5,720,714 A * | 2/1998 | Penrose | ........................... 602/6 |

(Continued)

FOREIGN PATENT DOCUMENTS

DE       296 18 426 U1    2/1997

Primary Examiner — Victoria J Hicks
(74) Attorney, Agent, or Firm — Young & Thompson

(57) ABSTRACT

A device (1) includes a first web of soft material (5), a projecting structure integral with the web and including multiple discrete projecting elements. The projecting elements include pieces of foam (3) spaced apart form one another and integral with the first web (5). The pieces of foam are compressed between the first web (5) and a second web (7) of soft material, the two webs mutually adhering between the projecting elements. The device is useful for treating various types of edemas and excessive tissue infiltration, as well as for repairing sports injury.

21 Claims, 8 Drawing Sheets

(56) References Cited

U.S. PATENT DOCUMENTS 6,656,141 B1    12/2003  Reid
6,808,791 B2 *  10/2004  Curro .................... A47L 1/15
                                                   239/53

* cited by examiner

DEVICE, STRAP AND GARMENT FOR TREATING SKIN AND SUBCUTANEOUS TISSUE DISORDERS AND FOR REPAIRING SPORTS INJURY, AND METHOD FOR MAKING SAME

The present invention relates to a device for treating skin and subcutaneous tissue disorders and for repairing sports injury, of the type comprising a first web of flexible material and a projecting structure which is joined to the web and comprises a plurality of discrete projecting elements, said projecting elements comprising pieces of foam which are spaced apart from one another and are joined to said first web.

There are various known devices of that type, such as foam pads from one face of which hemispherical forms project (DE-296 18 426 U1). In other known devices, a textile surface or a flexible material carries half-spheres which have a very small radius of curvature, from 1 mm to 5 mm, and are constituted by a relatively hard material.

However, such devices exhibit disappointing therapeutic results and are poorly tolerated by patients owing to allergies or a lack of comfort.

The object of the invention is to improve the effectiveness of the treatment of skin and subcutaneous tissue disorders by means of a device which is well tolerated by patients.

To that end, the invention relates to a device of the above-mentioned type, characterized in that the pieces of foam are compressed between said first web and a second web of flexible material, the two webs adhering together between the projecting elements.

Other features of the device are described in claims 2 to 15.

The invention relates also to a piece of foam for a treatment device as defined above, characterized in that it comprises a first end layer with high indentation and a second end layer with low indentation.

According to an embodiment, the piece of foam is composed of two superposed elements which are constituted by different foams and are joined to one another, namely a first element of foam with low indentation and a second element of foam with high indentation.

The invention relates also to:
a strap for treating skin and subcutaneous tissue disorders and for repairing sports injury, comprising a device as defined above bordered by two edges which do not have projecting elements;
a garment for treating skin and subcutaneous tissue disorders and for repairing sports injury, comprising a device as defined above on at least a portion of its inside surface; and
a method for producing a device as defined above, characterized in that said first web is advanced on a substantially horizontal plane, the pieces of foam are dropped at regular intervals onto said first web as it advances and are fixed thereto, and said second web of flexible material is applied to the pieces of foam so that it compresses the pieces of foam and adheres to said first web between the pieces.

In a mode of implementation, strips of foam are moved forward in parallel chutes which open into a supply zone, and the strips of foam are cut at regular intervals to form the pieces of foam, which fall onto said first web as it advances.

The invention will be better understood upon reading the following description, which is given solely by way of example and with reference to the accompanying drawings, in which.

Figure 1:
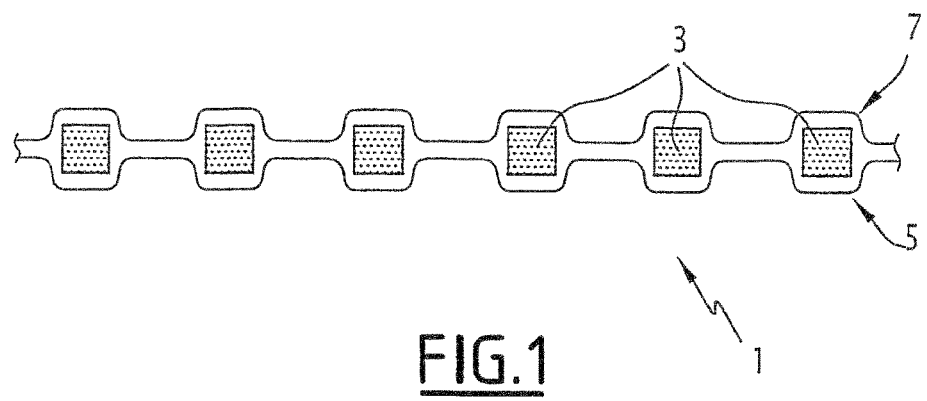
FIG. 1 is a cross-sectional view of a device according to the invention.
Figure 2:
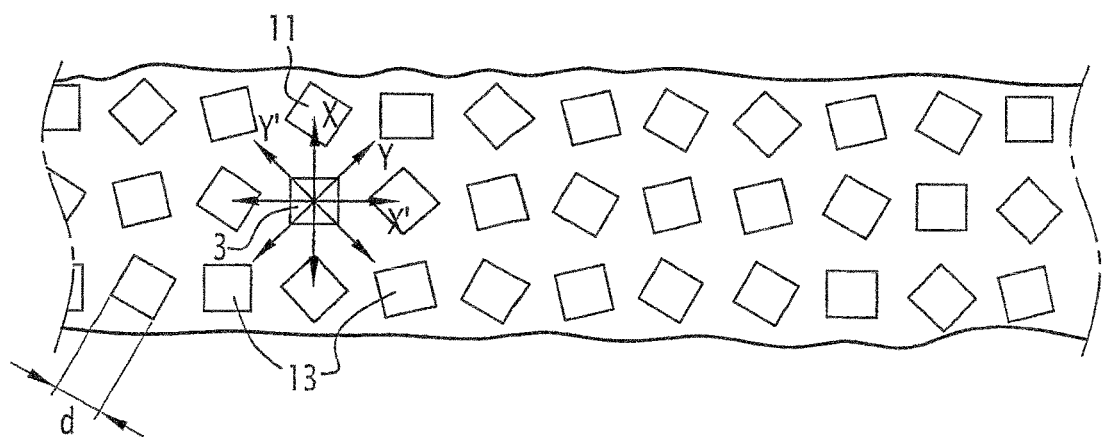
FIG. 2 is a top view of the device of FIG. 1.

The device 1 shown in FIGS. 1 and 2 is to be placed on the skin beneath a compression or retaining bandage in order to treat skin or subcutaneous tissue disorders and, in particular, to treat various types of edema or excessive tissue infiltration. In that case, the device is said to be reducing. The device can also be used for repairing sports injury after strain. The device 1 substantially comprises blocks of foam 3 which are spaced apart from one another and are compressed between two webs of flexible material 5 and 7. The two webs adhere to one another between the blocks of foam.

In the embodiment shown, the blocks are obtained from a sheet of cast latex foam which is able to expand freely so as to form a lightweight foam having open cells. The foam is very resilient so that it is able to adapt to the shape of any body surface against which it is pressed. The indentation of the foam can vary according to the pathologies and the area of the body to which the device 1 is applied, as is shown by the table below. In general, the indentation is from 200 to 250 N, but it can also be higher on healthy skin, for use in the repair of sports injury. The density of the foam can vary in a range of from 13 to 100 kg/m$^3$.

As is well known, indentation is a method of measuring the hardness by indentation of flexible alveolar materials. The indentation value is the force applied for a penetration of 40% of an indenter, under standardized conditions described in standard ISO2439 of September 1997.

| Foam indentation values as a function of the type of pathology | |
|---|---|
| | Edemas of soft texture on fragile skin or particularly painful edemas: |
| Low indentation | post-surgical edemas (orthopedic surgery, etc.) edemas following liposuction traumatic edemas (sprain) cardiac or renal edemas which affect the lower limbs inflammatory edemas (algodystrophy, gonarthrosis, etc.) allergic edemas edemas of burns in the acute phase |
| Medium indentation | edemas of stases edemas of venous, acute or chronic insufficiency (phlebitis, hypodermitis,) fatty edemas, cellulite, excess weight, edemas of peripheral neurological origin (plexitis due to irradiation) edemas of central origin: hemiplegia, paraplegia, etc. incipient lymphedemas |
| High indentation | constituted lymphedemas elephantiasis all healthy fibrous tissues all cheloid scars (if they are not inflammatory) ulcers which are neither infected nor inflammatory ochre dermatitis |

| Foam indentation values as a function of the area of the body | |
|---|---|
| | All visible osseous reliefs (Achilles tendon, tibial crest, clavicle, etc.) and all areas where the lymphatic ganglions are palpable |
| Low indentation | knee neck of the foot crease of the groin antero-internal face of the thigh antero-internal face of the arm elbow axillary hollow, etc. |
| High indentation | top of the foot back of the lateral and medial malleolus outside surface of the thigh, hip, buttocks, back in general, pubis and virtually the whole of the leg (except the tibial crest) back of the hand forearm ext and post face of the arm the toes |

The size and shape of the blocks vary according to the pathology and the area of the body against which the device is pressed. In the embodiment shown, the pieces of foam are in the form of regular blocks of height h and substantially square cross-section, of side d. Their height h preferably varies from 8 to 12 mm and the cross-sectional area varies from 25 mm$^2$ for the fingers and toes to 900 mm$^2$ for the back or the abdomen, passing through 100 mm$^2$ for the hand and 400 mm$^2$ for the arm or thigh. In another embodiment, the blocks are parallelepipeds in the form of elongated tongues, one of the dimensions of which is very much greater than the others.

The flexible material used for the webs 5 and 7 can be, for example, an adhesivated polyester nonwoven which has a density of 50 g/m$^2$ and has intrinsic elasticity in one direction. By way of variation, it can be a polyurethane nonwoven in two directions orthogonal with respect to one another, or a multidirectional elastic woven material.

FIG. 2 shows the distribution of the blocks of foam relative to one another in the plane of one of the two webs. The blocks of foam are aligned substantially according to regular rows parallel to a direction X, but their orientation is irregular relative to the axis of symmetry of each cube perpendicular to the plane of the web.

Each block 3 is at a distance of from d/2 to d from a first group of four immediately adjacent blocks 11 and at a distance of the order of 2d from a second group of four immediately adjacent blocks 13. The pieces 3 and 11 are aligned substantially according to the direction X and according to a direction X' substantially orthogonal to X, and the pieces 3 and 13 are aligned in two directions Y and Y' which are substantially orthogonal to each other and are inclined by approximately 45° relative to the directions X and X'.

Figure 11:
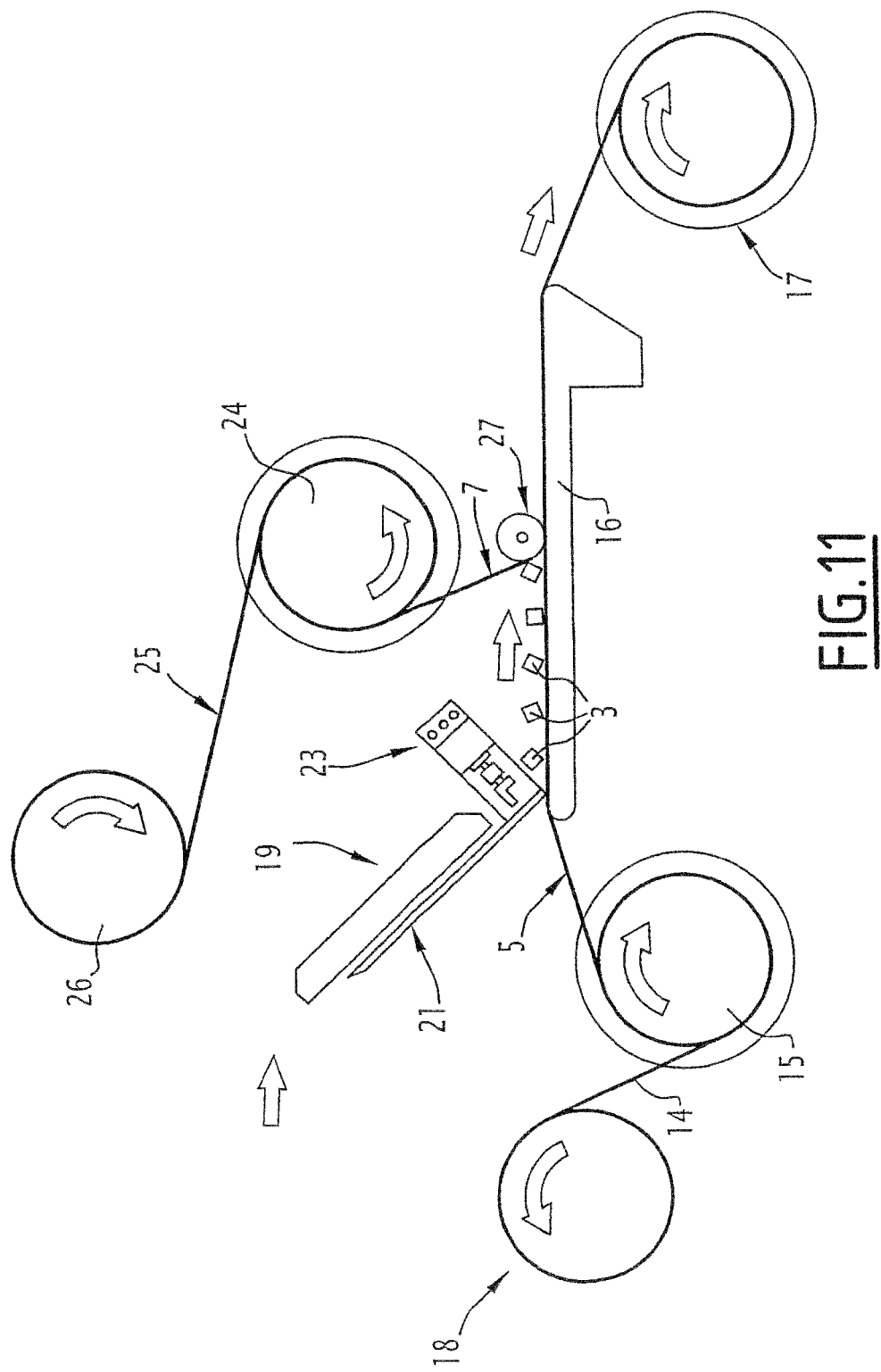
FIG. 11 is a cross-sectional view, in diagrammatic form, showing a method for producing the device of FIGS. 1 and 2.

That arrangement can be obtained by the production method described in FIG. 11. The first web 5 of adhesivated flexible material, which is covered with a temporary protective film 14 and wound on a supply spool 15, is spread out on a flat horizontal support 16 and advances horizontally, pulled by a receiving spool 17. Upstream of the support 16, the sheet 14 is wound on another spool 18. A block supply zone 19 is defined at the upstream end of the support 16. The supply zone contains several strips of foam which are aligned in parallel chutes and are cut into blocks by a guillotine 23.

The blocks fall at an adjustable frequency, and their height of fall is also adjustable. The frequency of fall determines the spacing of the cubes on the support web 5 as it advances. The height of fall determines the orientation of the blocks, which will be less regular as the height increases.

As the blocks fall, they become fixed to the adhesive web 5. The second web of flexible material 7, which is unwound from a spool 24, is likewise adhesivated and protected temporarily by a film 25, which is collected on a spool 26. The web 7 is then applied to the blocks of foam by a calendering roller 27. As it compresses the blocks of foam 3, it adheres to the first support web 5 between them.

Figure 12:
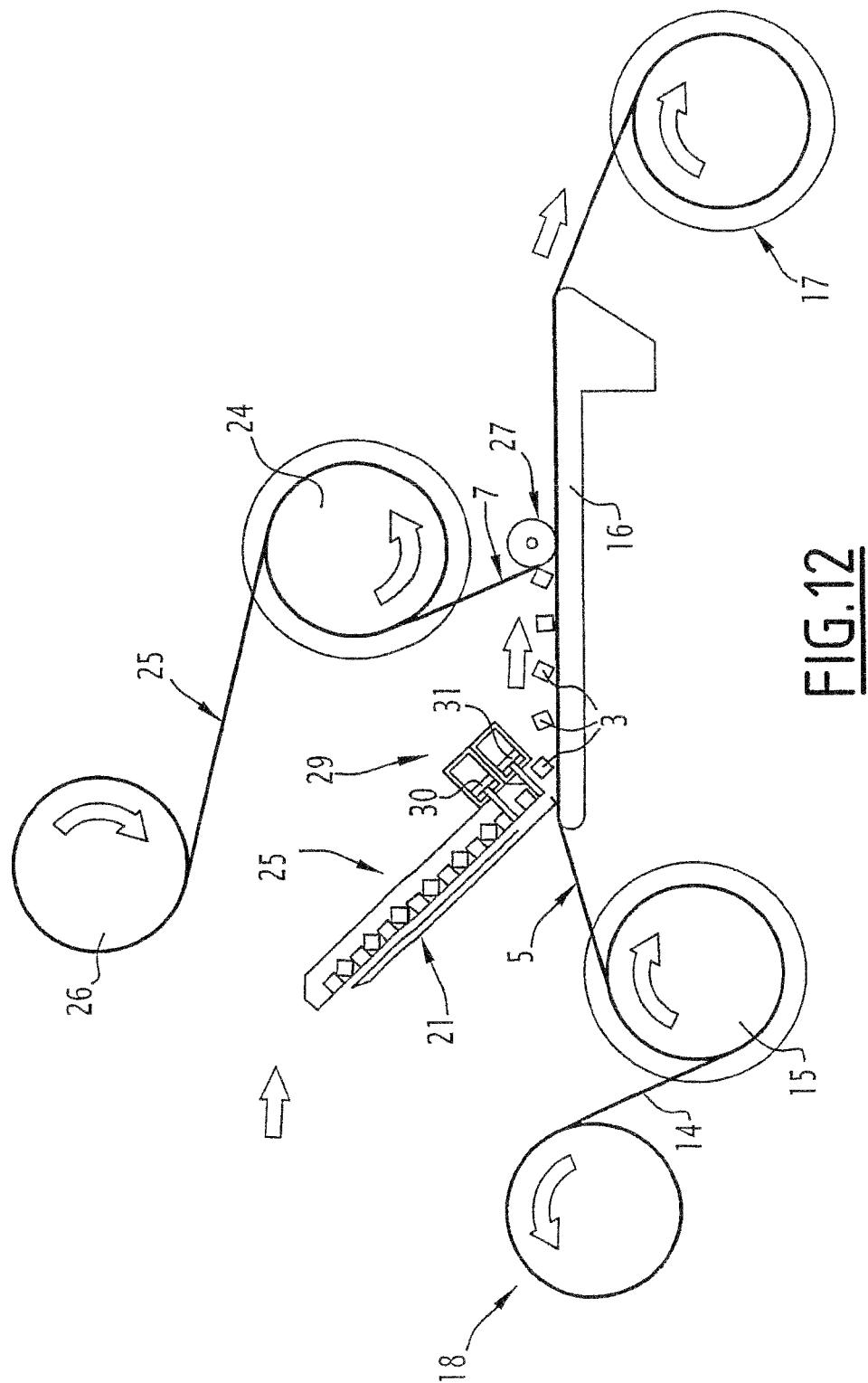
FIG. 12 is a cross-sectional view, in diagrammatic form, of a second method for producing the device of FIGS. 1 and 2.

In another embodiment (FIG. 12), the supply zone contains blocks of foam which are pre-cut in the chutes 21 and are distributed by a distributor/metering device 29, for example having two doors 30, 31 which move alternately.

The methods described above are suitable for permitting the production of the device 1 in the form of a sheet, for example having a length of 5 meters and a width of 30 cm, or alternatively in the form of a strap of the same length and having a width of 10 cm.

In both cases, cut piece of sheet or strap, the device 1 can be held against the skin by means of a compression strip, for example of FLEXIDEAL®, which holds the device against the skin, or alternatively by a compression bandage, for example of BIFLEX®, which, in addition to holding the device, exerts a pressure to a greater or lesser degree, which compresses the device against the skin. The type of strip used, rigid or elastic, for the reducing bandage depends on the pressure required for the pathology that is being treated.

The sheet is intended to be cut by a practitioner, who will adapt it to the area of tissue to be treated.

Figure 3:
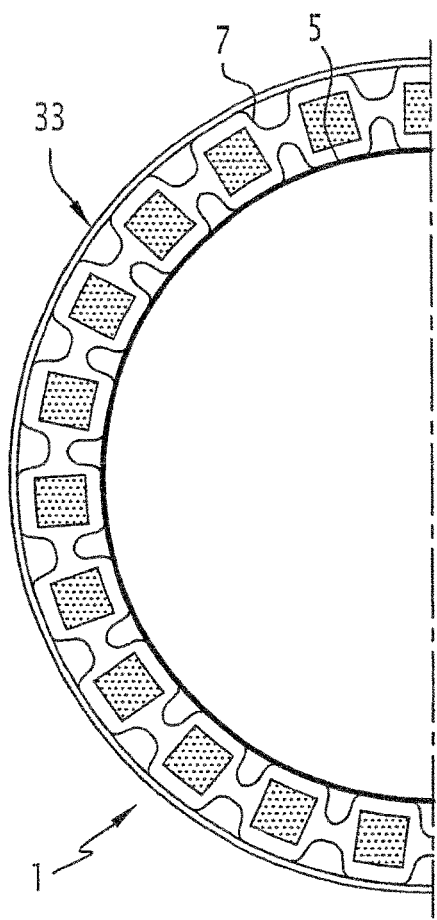
FIGS. 3 and 4 are cross-sectional views of the fitting of the device in bandage form around an arm.

FIG. 3 shows the use of the device in sheet form on an arm, without appreciable compression. The device 1 is held by a dressing in the form of a circular net 33. This assembly acts very rapidly on edemas of vascular origin, which are most of the time very soft, as well as on lymphedemas, especially fluid lymphedemas.

Figure 4:
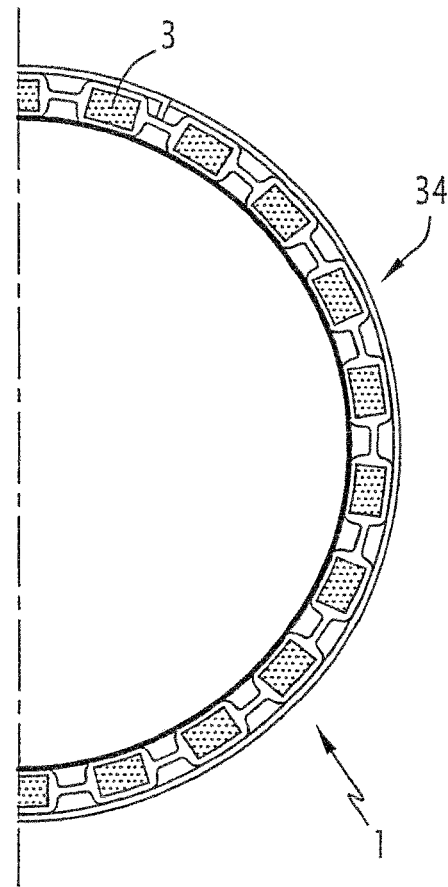

FIG. 4 shows a cross-sectional view of the use of the same device on an arm, with compression. In that case, the device 1 is held by a compression bandage 34, which maintains a substantial pressure on the cubes of foam, which are much more compressed. That use of the device is carried out in the case of very fibrous lymphedemas.

Figure 5:
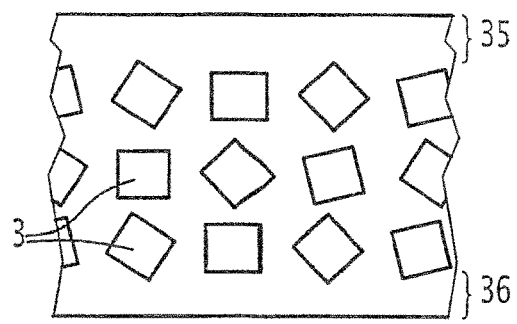
FIG. 5 is a top view of another device according to the invention, in strap form, the top web being shown transparent.
Figure 6:
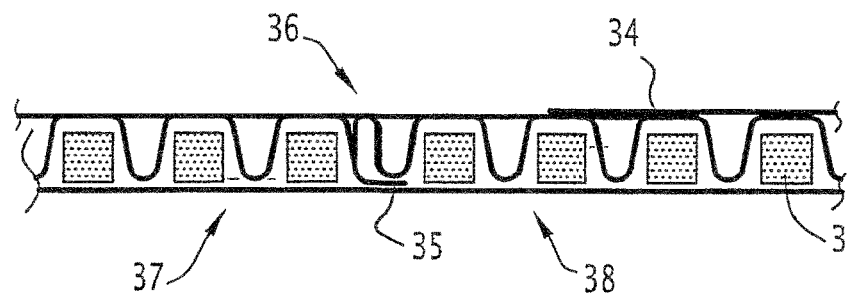
FIG. 6 is a cross-sectional view of the fitting of the device of FIG. 5.
Figure 7:
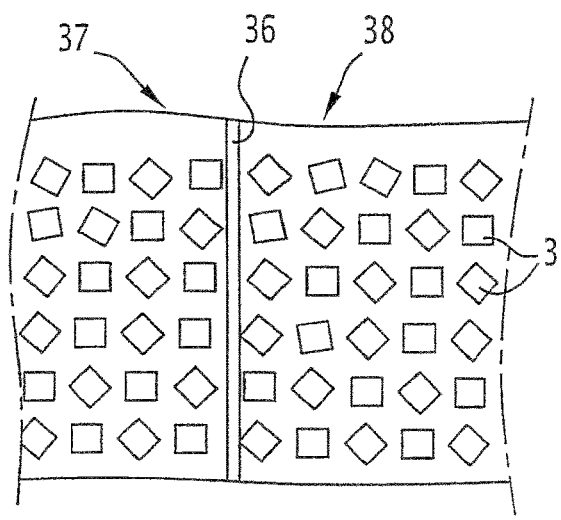
FIG. 7 is a top view of the object of FIG. 6, the retaining bandage having been removed, the top web being shown transparent.
Figure 8:
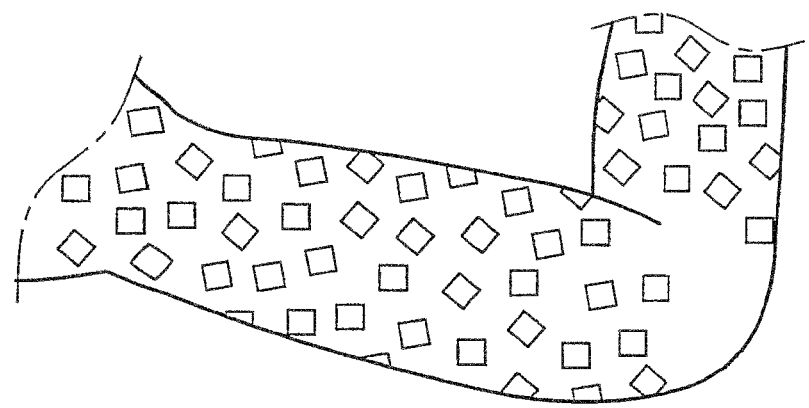
FIG. 8 is a perspective view of the impact of the device on the arm when the device is removed.

The strap (FIG. 5) is to be used to make a bandage around a limb. In the case of the strap, the production process will provide along the strap two edges 35 and 36 which do not have blocks of foam. The edges are used when bandaging a limb, as is shown in FIGS. 6 and 7. The advantage of the strap is that it can be adapted to the reduction in volume that it causes and that, owing to its simplicity, it can be used by the patient himself. The edge serves as a guide for the juxtaposition of the different bandage turns. FIG. 6 shows, in cross-sectional view, two bandage turns 37 and 38. The edge portion 35 of the bandage turn 37 serves as a guide for the bandage turn 38. The edge portion 36 of which comes to rest on the adjacent blocks of the turn 37. FIG. 7 shows in a top view, in diagrammatic form, that the bandage so produced on the arm is substantially homogeneous with regard to the distribution of the blocks of foam.

The device 1 can also be used in the form of a compression garment. The advantage of the compression garment is that it renders treatment much more bearable for the patient. The patient will accordingly be more disposed to follow his treatment, which will therefore be more effective.

Figure 10A:
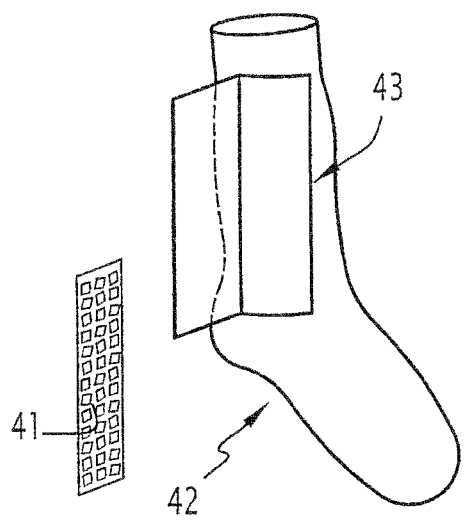
FIGS. 10A to 10C are perspective views describing the method for producing a sock including the device according to the invention.
Figure 10B:
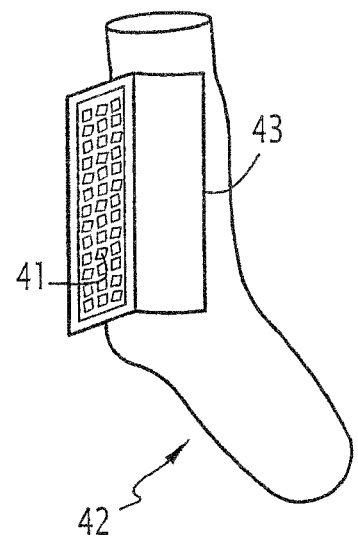
Figure 10C:
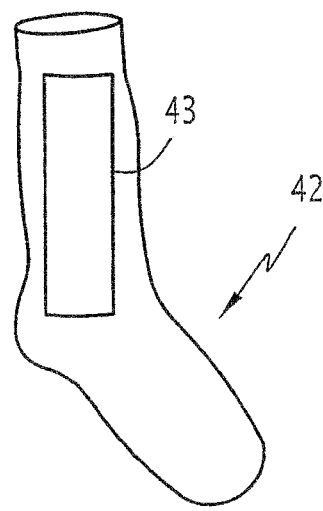

An embodiment of a garment associated with the device 1 is shown in FIGS. 10A to 10C: the device 1, in the form of a cut piece 41 of sheet or strap is inserted into a garment 42 which has been cut along a generating line 43. The piece 41 is sown inside the garment at the location where the treatment is to be applied. The garment is finally sown up along the generating line 43.

The garment can be especially a sports sock, stocking or tights, or briefs for various uses. The briefs can likewise be used for anti-cellulite treatment.

Figure 9:
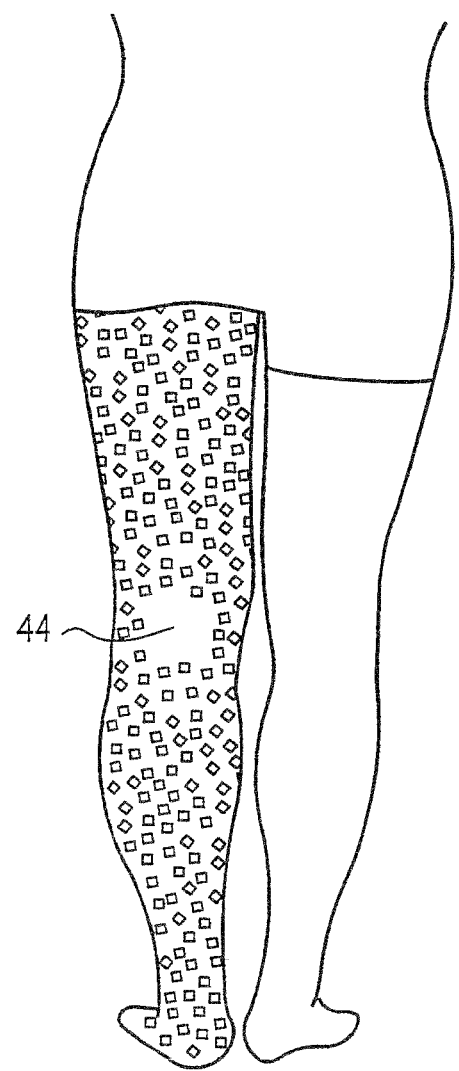
FIG. 9 is a perspective view of the legs of a patient showing the impact of the fitting of the device in bandage form around one of the legs when the device has been removed.

As a precaution, the inside of the garment should not be covered with the device in areas of articulation such as the knee and the popliteal hollow 44 in the case of a stocking that comes up over the knee (FIG. 9).

That type of garment can be made-to-measure, advantageously being designed by CAD (computer-assisted design) and then cut and sown, or can be produced by means of a digitally-controlled circular knitting machine operated by a software program capable of adjusting the compression by its adaptability to the patient's measurements, which are stored in a memory.

The reducing bandage is all the more effective it the pressure of the device against the skin is great, if it is worn for a long time and if muscular activity is associated therewith.

The pressure can be increased by a compression fitting and/or by muscular activity of the limb on which the bandage is applied.

The time for which the patient wears the bandage can be increased, because the device is well tolerated and simple to use. The patient's tolerance of the device, associated with a low-compression bandage or a made-to-measure garment, allows the patient to wear the device during his sleep, for example.

FIGS. 9 and 10 show the marks of the blocks on the skin after the reducing bandage has been removed from an arm (FIG. 9) and a leg (FIG. 10). The edges of the blocks of foam pressed against the skin act by a shearing effect on the skin, massage it, allowing the surface microcirculation in the region of the superficial cutaneous network to be increased and, in the case of lymphatic edemas, allowing softening of the subjacent skin elements to begin. The shearing effect consists in moving the tissues relative to one another, in promoting sliding planes in order to reach the deeper layers of the cutaneous network. Owing to the different distances between immediately adjacent pieces of foam and the elasticity of the webs 5 and 7, different pressures exerted on the subjacent tissue have the effect of reducing the stiffness and immobility thereof.

The shearing effect thus renders the pressure much more effective, which results in the drainage of the fluids towards the superficial collectors then the deeper collectors of the lymphatic network. The pressure effect is made effective by the small distance separating each piece of foam from the first group of adjacent pieces, while the shearing effect, linked with the freedom of movement of the blocks, is promoted by the large distance separating each block from the second group of adjacent blocks, and by the elasticity of the webs 5 and 7.

Accordingly, the device according to the invention has a double effect, of shearing and of draining self-massage, which is particularly beneficial for circulation in the cutaneous and subcutaneous region.

That essential double action is all the more effective because the treatment is well tolerated by patients owing to the production processes between two webs. The device can also be used at night, in the form of a garment or low-compression bandage, which promotes good patient compliance with the treatment.

Figure 14:
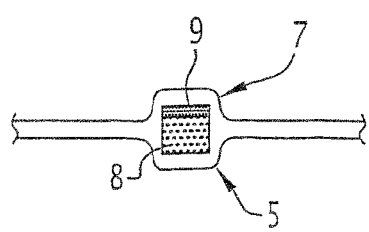
FIG. 14 is a cross-sectional view of the device in a particular embodiment in which the pieces are composed of two different foams.

In another embodiment, shown in FIG. 14, each piece of foam is composed of two superposed elements constituted by different foams, the first element 8 made of a foam with high indentation on the side of one of the webs of flexible material 5 and the second element 9 of a foam with low indentation, bonded to the element 8 on the side of the other web of flexible material 7. The elements 8 and 9 can be bonded to one another. By way of variation, by means of an appropriate foaming process, it is possible to obtain blocks in which the indentation varies continuously from one face to the other.

The advantage of that embodiment is that the distribution of the retaining/compression force is improved, the compression force being applied on the face with low indentation, without making the blocks more aggressive towards the patient's skin.

Figure 13:
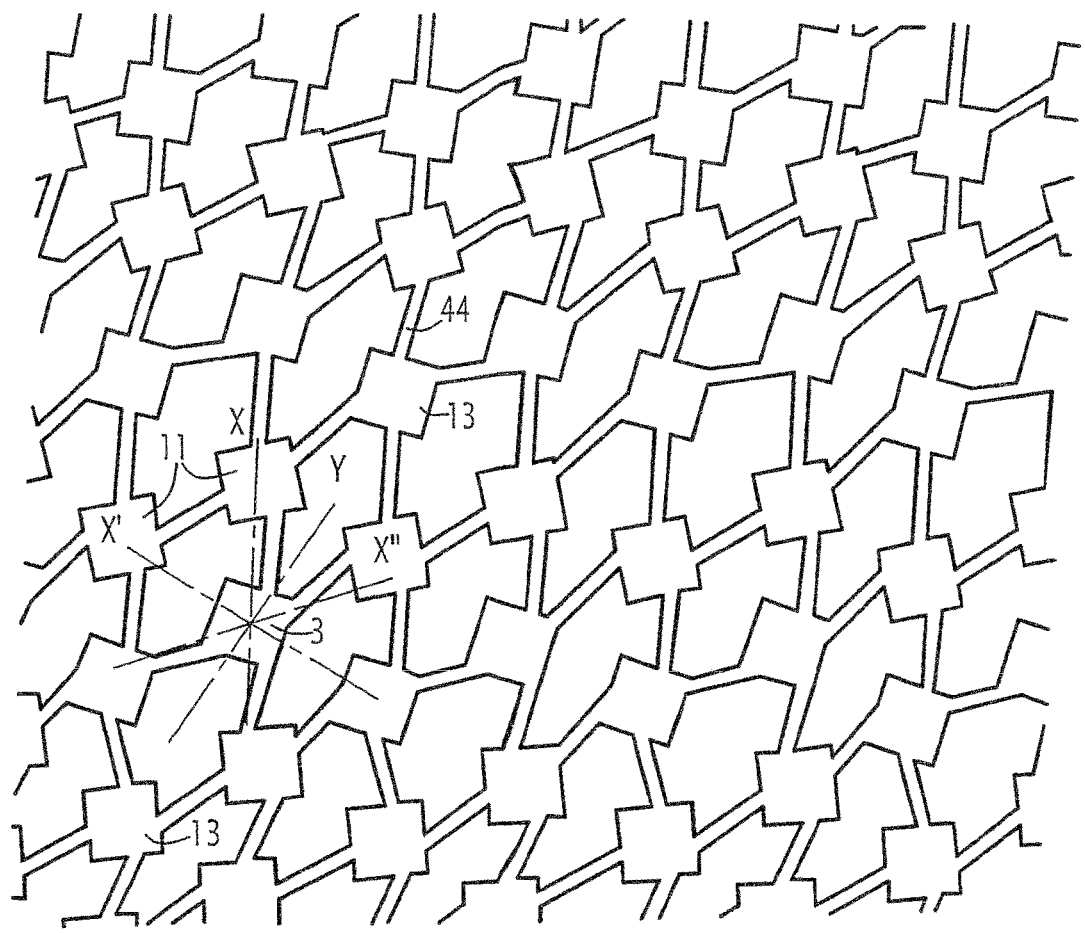
FIG. 13 is a top view, in diagrammatic form, of a variant of the device according to the invention.

FIG. 13 shows another embodiment in which the blocks are staggered from one row according to direction X to the next row, each block being joined to four of its closest neighbours by a foam joining element 44. That arrangement of the blocks can be obtained by punching a sheet of foam out.

In that case, each block 3 has six close neighbours 11, aligned according to three directions X, X' and X", and two substantially more distant neighbours 13, which are aligned according to a direction Y which lies between the directions X and X".

The invention claimed is:
1. A wearable item for treating skin and subcutaneous tissue disorders, comprising a device comprising:
    a first web of flexible material;
    a second web of flexible material; and
    a projecting structure which is joined to the first web and comprises a plurality of discrete projecting elements, said discrete projecting elements comprising parallelepiped pieces of foam which are spaced apart from one another and are joined to said first web;
    wherein the device is bordered by two edges which do not have said discrete projecting elements,
    wherein the parallelepiped pieces of foam are reduced in volume by pressure exerted upon them by said first web and said second web, the first and second webs adhering directly to each other between the discrete projecting elements, and wherein the parallelepiped pieces of foam have respective orientations that are irregular relative to an axis of symmetry of each of the parallelepiped pieces of foam perpendicular to a plane of one of said first and second webs, wherein the wearable item further comprises a compression band or a compression bandage that is capable of pressing the device against the skin.

2. The wearable item according to claim 1, wherein, over at least a portion of a surface of the device, a distance separating one of said parallelepiped pieces of foam from a second group of immediately adjacent said parallelepiped pieces of foam is several times greater than a distance separating the one of said parallelepiped pieces of foam from a first group of immediately adjacent said parallelepiped pieces of foam.

3. The wearable item according to claim 2, wherein the parallelepiped pieces of foam of said first group are aligned in first and second directions, and the parallelepiped pieces of foam of said second group are aligned in at least one further direction that lies between said first and second directions.

4. The wearable item according to claim 3, wherein said first and second directions are substantially orthogonal to each other, and the parallelepiped pieces of foam of said second group are in two said further directions that are substantially orthogonal to each other.

5. The wearable item according to claim 2, wherein, on said at least one portion of the surface of the device, the one of said parallelepiped pieces of foam is at a distance of an order of a fraction of d or close to d from said first group of immediately adjacent said parallelepiped pieces of foam and at a distance of an order of a multiple of d from said second group of immediately adjacent said parallelepiped pieces of foam, d being an average size of said parallelepiped pieces of foam in the plane of said first web.

6. The wearable item according to claim 1, wherein each of said parallelepiped pieces of foam comprises a first end layer with high indentation and a second end layer with low indentation.

7. The wearable item according to claim 6, wherein each of said parallelepiped pieces of foam is composed of two superposed elements which are constituted by different foams and are joined to one another, namely a first element of foam with low indentation and a second element of foam with high indentation.

8. The wearable item according to claim 1, wherein the parallelepiped pieces of foam comprise a foam with open cells.

9. The wearable item according to claim 1, wherein the parallelepiped pieces of foam have, seen from a top, two dimensions similar to each other.

10. The wearable item according to claim 1, wherein the parallelepiped pieces of foam are tongue-shaped, wherein a dimension in a longitudinal direction is very much greater than a dimension in a latitudinal direction.

11. The wearable item according to claim 1, wherein at least one of said first and second webs is made of a nonwoven material having intrinsic elasticity in at least one direction.

12. The wearable item according to claim 1, wherein at least one of said first and second webs is made of an elastic woven material having multidirectional elasticity.

13. The wearable item according to claim 1, wherein the parallelepiped pieces of foam have an indentation having a value of from 200 N to 250 N.

14. The wearable item according to claim 1, wherein the discrete projecting elements are joined together by joining elements formed in one piece therewith.

15. A wearable item for treating skin and subcutaneous tissue disorders, comprising a device comprising:
a first web of flexible material;
a second web of flexible material; and
a projecting structure which is joined to the first web and comprises a plurality of discrete projecting elements, said discrete projecting elements comprising parallelepiped pieces of foam which are spaced apart from one another and are joined to said first web;
wherein the device is bordered by two edges which do not have said discrete projecting elements,
wherein the parallelepiped pieces of foam are reduced in volume by pressure exerted upon them by said first web and said second web, the first and second webs adhering directly to each other between the discrete projecting elements, and
wherein the parallelepiped pieces of foam have respective orientations that are irregular relative to an axis of symmetry of each of the parallelepiped pieces of foam perpendicular to a plane of one of said first and second webs,
wherein the wearable item consists of a compression garment.

16. The wearable item according to claim 15, wherein the parallelepiped pieces of foam comprise a foam with open cells.

17. The wearable item according to claim 15, wherein, over at least a portion of a surface of the device, a distance separating one of said parallelepiped pieces of foam from a second group of immediately adjacent said parallelepiped pieces of foam is several times greater than a distance separating the one of said parallelepiped pieces of foam from a first group of immediately adjacent said parallelepiped pieces of foam.

18. The wearable item according to claim 15, wherein the parallelepiped pieces of foam have an indentation having a value of from 200 N to 250 N.

19. The wearable item according to claim 15, wherein the compression garment comprises at least one of: a sock, a stocking, tights, and a brief.

20. Method for producing a device comprising:
a first web of flexible material;
a second web of flexible material; and
a projecting structure which is joined to the first web and comprises a plurality of discrete projecting elements, said discrete projecting elements comprising parallelepiped pieces of foam which are spaced apart from one another and are joined to said first web,
wherein the parallelepiped pieces of foam are compressed between said first web and said second web, the first and second webs adhering to each other between the discrete projecting elements,
wherein the parallelepiped pieces of foam have respective orientations that are irregular relative to an axis of symmetry of each of the parallelepiped pieces of foam perpendicular to a plane of one of said first and second webs,
the method comprising the steps of:
advancing said first web on a substantially horizontal plane, dropping the parallelepiped pieces of foam at regular intervals onto said first web as it advances and fixing the parallelepiped pieces of foam to said first web, and applying said second web of flexible material to the parallelepiped pieces of foam so that said second web compresses the parallelepiped pieces of foam and adheres to said first web between the parallelepiped pieces of foam, whereby the parallelepiped pieces of foam have respective orientations that are irregular relative to an axis of symmetry of each of the parallelepiped pieces of foam perpendicular to a plane of one of said first and second webs.

21. Production method according to claim 20, further comprising moving strips of foam forward in parallel chutes which open into a supply zone, cutting the strips of foam at regular intervals to form the parallelepiped pieces of foam, and allowing the parallelepiped pieces of foam to fall onto said first web as said first web advances.

\* \* \* \* \*